(12) United States Patent
Baker, Jr.

(10) Patent No.: US 8,123,695 B2
(45) Date of Patent: Feb. 28, 2012

(54) METHOD AND APPARATUS FOR DETECTION OF VENOUS PULSATION

(75) Inventor: Clark R. Baker, Jr., Newman, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1554 days.

(21) Appl. No.: 11/528,295

(22) Filed: Sep. 27, 2006

(65) Prior Publication Data

US 2008/0077022 A1  Mar. 27, 2008

(51) Int. Cl.
*A61B 5/02* (2006.01)
(52) U.S. Cl. ......... 600/500; 600/323; 600/501; 600/300
(58) Field of Classification Search .......... 600/323–324, 600/500–504; 702/189–194
See application file for complete search history.

(56) References Cited

U.S. PATENT DOCUMENTS 4,380,439 A  4/1983  Kreitenberg
(Continued)

FOREIGN PATENT DOCUMENTS

CN  1642472  7/2005
(Continued)

OTHER PUBLICATIONS

Shelley et al. "The Detection of Peripheral Venous Pulsation Using the Pulse Oximeter as a Plethysmograph," 1993, J Clin Monit; 9, pp. 283-287.*
Shelley et al., "The Effect of Venous Pulsation on the Forehead Pulse Oximeter Wave Form as a Possible Source of Error in SpO2 Calculation" 2005 Anesth Analg; 100, pp. 743-747.*

(Continued)

*Primary Examiner* — Miranda Le
*Assistant Examiner* — Eric Messersmith

(57) ABSTRACT

Methods and systems for detecting venous pulsation are provided. In one embodiment, a metric of the pulse shape of one or more plethysmographic signals is derived and the presence of venous pulsation is detected based on the metric of pulse shape. Examples, of metrics of pulse shape include a skew metric and a ratio of a minima-to-maxima time over a pulse period interval. In an exemplary embodiment, the presence of venous pulsation is detected based on a metric of the pulse shape of one or more plethysmographic signals and on a phase comparison of the plethysmographic signals.

9 Claims, 5 Drawing Sheets

U.S. PATENT DOCUMENTS

| | | | |
|---|---|---|---|
| 4,759,369 A | 7/1988 | Taylor | |
| 4,824,242 A | 4/1989 | Frick et al. | |
| 4,854,699 A | 8/1989 | Edgar et al. | |
| 4,859,057 A | 8/1989 | Taylor et al. | |
| 4,863,265 A | 9/1989 | Flower et al. | |
| 4,867,557 A | 9/1989 | Takatani et al. | |
| 4,907,594 A | 3/1990 | Muz | |
| 4,911,167 A | 3/1990 | Corenman et al. | |
| 4,926,867 A | 5/1990 | Kanda et al. | |
| 4,955,379 A | 9/1990 | Hall | |
| 4,968,137 A | 11/1990 | Yount | |
| 5,025,791 A | 6/1991 | Niwa | |
| 5,251,632 A | 10/1993 | Delpy | |
| 5,263,244 A | 11/1993 | Centa et al. | |
| 5,267,562 A | 12/1993 | Ukawa et al. | |
| 5,267,563 A | 12/1993 | Swedlow et al. | |
| 5,278,627 A | 1/1994 | Aoyagi et al. | |
| 5,297,548 A | 3/1994 | Pologe | |
| 5,299,120 A | 3/1994 | Kaestle | |
| 5,329,922 A | 7/1994 | Atlee, III | |
| 5,348,005 A | 9/1994 | Merrick et al. | |
| 5,349,519 A | 9/1994 | Kaestle | |
| 5,355,882 A | 10/1994 | Ukawa et al. | |
| 5,390,670 A | 2/1995 | Centa et al. | |
| 5,392,777 A | 2/1995 | Swedlow et al. | |
| 5,396,893 A | 3/1995 | Oberg et al. | |
| 5,402,777 A | 4/1995 | Warring et al. | |
| 5,402,778 A | 4/1995 | Chance | |
| 5,408,998 A | 4/1995 | Mersch | |
| 5,417,207 A | 5/1995 | Young et al. | |
| 5,458,562 A | 10/1995 | Cooper | |
| 5,485,847 A | 1/1996 | Baker, Jr. | |
| 5,490,505 A | 2/1996 | Diab et al. | |
| 5,503,148 A | 4/1996 | Pologe et al. | |
| 5,517,988 A | 5/1996 | Gerhard | |
| 5,522,388 A | 6/1996 | Ishikawa et al. | |
| 5,524,617 A | 6/1996 | Mannheimer | |
| 5,575,285 A | 11/1996 | Takanashi et al. | |
| 5,584,299 A | 12/1996 | Sakai et al. | |
| 5,595,176 A | 1/1997 | Yamaura | |
| 5,645,059 A | 7/1997 | Fein et al. | |
| 5,662,106 A | 9/1997 | Swedlow et al. | |
| 5,685,299 A | 11/1997 | Diab et al. | |
| 5,690,104 A | 11/1997 | Kanemoto et al. | |
| 5,715,816 A | 2/1998 | Mainiero et al. | |
| 5,743,261 A | 4/1998 | Mainiero et al. | |
| 5,743,263 A | 4/1998 | Baker, Jr. | |
| 5,743,349 A | 4/1998 | Steinberg | |
| 5,746,206 A | 5/1998 | Mannheimer | |
| 5,766,127 A | 6/1998 | Pologe et al. | |
| 5,810,723 A | 9/1998 | Aldrich | |
| 5,817,008 A | 10/1998 | Rafert et al. | |
| 5,830,137 A | 11/1998 | Scharf | |
| 5,853,364 A | 12/1998 | Baker, Jr. et al. | |
| 5,871,694 A | 2/1999 | Beden et al. | |
| 5,891,025 A | 4/1999 | Buschmann et al. | |
| 5,902,235 A | 5/1999 | Lewis et al. | |
| 5,934,277 A | 8/1999 | Mortz | |
| 6,018,673 A | 1/2000 | Chin et al. | |
| 6,035,223 A * | 3/2000 | Baker, Jr. | 600/323 |
| 6,073,041 A | 6/2000 | Hu et al. | |
| 6,149,597 A | 11/2000 | Kamiyama | |
| 6,151,107 A | 11/2000 | Schollermann et al. | |
| 6,151,516 A | 11/2000 | Kiani-Azarbayjany et al. | |
| 6,151,518 A | 11/2000 | Hayashi | |
| 6,178,343 B1 | 1/2001 | Bindszus et al. | |
| 6,216,021 B1 | 4/2001 | Franceschini et al. | |
| 6,222,189 B1 | 4/2001 | Misner et al. | |
| 6,230,035 B1 | 5/2001 | Aoyagi et al. | |
| 6,258,038 B1 | 7/2001 | Haryadi et al. | |
| 6,263,222 B1 | 7/2001 | Diab et al. | |
| 6,272,363 B1 | 8/2001 | Casciani et al. | |
| 6,278,889 B1 | 8/2001 | Robinson | |
| 6,285,896 B1 | 9/2001 | Tobler et al. | |
| 6,299,583 B1 | 10/2001 | Eggers et al. | |
| 6,330,468 B1 | 12/2001 | Scharf | |
| 6,334,065 B1 | 12/2001 | Al-Ali et al. | |
| 6,339,715 B1 | 1/2002 | Bahr et al. | |
| 6,374,129 B1 | 4/2002 | Chin et al. | |
| 6,381,480 B1 | 4/2002 | Stoddart et al. | |
| 6,385,471 B1 | 5/2002 | Mortz | |
| 6,393,310 B1 | 5/2002 | Kuenstner | |
| 6,393,311 B1 | 5/2002 | Edgar, Jr. et al. | |
| 6,397,093 B1 | 5/2002 | Aldrich | |
| 6,406,267 B1 | 6/2002 | Mondiere | |
| 6,411,832 B1 | 6/2002 | Guthermann | |
| 6,415,236 B2 | 7/2002 | Kobayashi et al. | |
| 6,438,399 B1 | 8/2002 | Kurth | |
| 6,449,501 B1 | 9/2002 | Reuss | |
| 6,461,165 B1 | 10/2002 | Takanashi et al. | |
| 6,480,729 B2 | 11/2002 | Stone | |
| 6,494,576 B1 | 12/2002 | L'Esperance | |
| 6,501,974 B2 | 12/2002 | Huiku | |
| 6,519,486 B1 | 2/2003 | Edgar, Jr. et al. | |
| 6,526,297 B1 | 2/2003 | Merilainen | |
| 6,584,336 B1 | 6/2003 | Ali et al. | |
| 6,587,704 B1 | 7/2003 | Fine et al. | |
| 6,606,509 B2 | 8/2003 | Schmitt | |
| 6,615,065 B1 | 9/2003 | Barrett et al. | |
| 6,622,095 B2 | 9/2003 | Kobayashi et al. | |
| 6,647,280 B2 | 11/2003 | Bahr et al. | |
| 6,650,917 B2 | 11/2003 | Diab et al. | |
| 6,671,526 B1 | 12/2003 | Aoyagi et al. | |
| 6,702,752 B2 | 3/2004 | Dekker | |
| 6,714,803 B1 | 3/2004 | Mortz | |
| 6,714,804 B2 | 3/2004 | Al-Ali et al. | |
| 6,754,515 B1 | 6/2004 | Pologe | |
| 6,770,028 B1 | 8/2004 | Ali et al. | |
| 6,780,158 B2 | 8/2004 | Yarita | |
| 6,801,799 B2 | 10/2004 | Mendelson | |
| 6,810,277 B2 | 10/2004 | Edgar, Jr. et al. | |
| 6,819,950 B2 | 11/2004 | Mills | |
| 6,839,585 B2 | 1/2005 | Lowery et al. | |
| 6,842,635 B1 | 1/2005 | Parker | |
| 6,845,256 B2 | 1/2005 | Chin et al. | |
| 6,859,658 B1 | 2/2005 | Krug | |
| 6,879,850 B2 | 4/2005 | Kimball | |
| 6,898,452 B2 | 5/2005 | Al-Ali et al. | |
| 6,947,780 B2 | 9/2005 | Scharf | |
| 6,947,781 B2 | 9/2005 | Asada et al. | |
| 6,970,792 B1 | 11/2005 | Diab | |
| 6,987,994 B1 | 1/2006 | Mort | |
| 7,039,538 B2 | 5/2006 | Baker, Jr. | |
| 7,194,293 B2 | 3/2007 | Baker, Jr. | |
| 7,206,621 B2 | 4/2007 | Aoyagi et al. | |
| 7,209,774 B2 | 4/2007 | Baker, Jr. | |
| 2004/0138538 A1 * | 7/2004 | Stetson | 600/310 |
| 2004/0230107 A1 | 11/2004 | Asada et al. | |
| 2004/0236196 A1 | 11/2004 | Diab et al. | |
| 2004/0249252 A1 | 12/2004 | Fine et al. | |
| 2005/0085702 A1 * | 4/2005 | Diab | 600/324 |
| 2005/0197552 A1 | 9/2005 | Baker, Jr. | |
| 2005/0197579 A1 | 9/2005 | Baker, Jr., et al. | |
| 2005/0256386 A1 | 11/2005 | Chan et al. | |
| 2006/0200015 A1 | 9/2006 | Baker, Jr. | |
| 2006/0224053 A1 | 10/2006 | Black et al. | |
| 2006/0253007 A1 | 11/2006 | Cheng et al. | |
| 2007/0077200 A1 | 4/2007 | Baker, Jr. | |
| 2007/0100220 A1 | 5/2007 | Baker, Jr. | |
| 2007/0142717 A1 | 6/2007 | Lowery et al. | |
| 2007/0208242 A1 | 9/2007 | Baker, Jr. | |

FOREIGN PATENT DOCUMENTS

| | | |
|---|---|---|
| DE | 69123448 | 5/1997 |
| JP | 63275325 | 11/1988 |
| JP | 2013450 | 1/1990 |
| JP | 2111343 | 4/1990 |
| JP | 4174648 | 6/1992 |
| JP | 2004008572 | 1/2004 |
| JP | 2004148070 | 5/2004 |
| JP | 2004166775 | 6/2004 |
| JP | 2005046234 | 2/2005 |
| JP | 2005095606 | 4/2005 |
| JP | 2005169020 | 6/2005 |
| JP | 2006075354 | 3/2006 |
| JP | 2006212161 | 8/2006 |
| JP | 2006325766 | 12/2006 |

| | | |
|---|---|---|
| JP | 3944448 | 7/2007 |
| JP | 2007295973 | 11/2007 |
| JP | 2007330708 | 12/2007 |
| JP | 4038280 | 1/2008 |
| WO | WO9200513 | 1/1992 |
| WO | WO9817174 | 4/1998 |
| WO | WO03039326 | 5/2003 |
| WO | WO2004006748 | 1/2004 |

OTHER PUBLICATIONS

Shelley et al. "What is the Best Site for Measuring the Effect of Ventilation on the Pulse Oximeter Waveform?" Aug. 2006, Anesth Analg; 103, pp. 372-377.*

Aoyagi, T., et al.; "Analysis of Motion Artifacts in Pulse Oximetry," *Japanese Society ME*, vol. 42, p. 20 (1993) (Article in Japanese—contains English summary of article).

Goldman, Julian M.; "Masimo Signal Extraction Pulse Oximetry," *Journal of Clinical Monitoring and Computing*, vol. 16, pp. 475-483 (2000).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

* cited by examiner

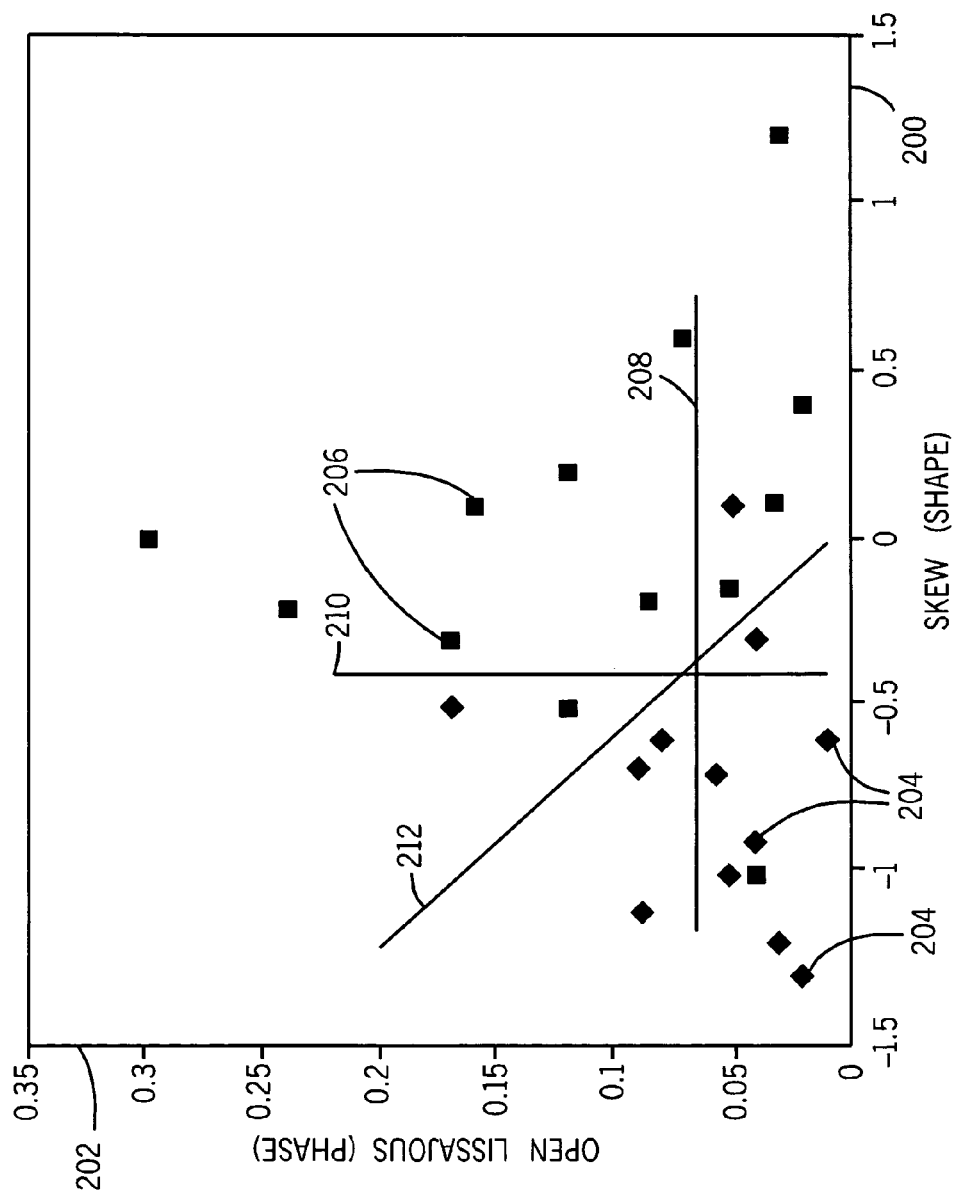

METHOD AND APPARATUS FOR DETECTION OF VENOUS PULSATION

BACKGROUND OF THE INVENTION

1. Field of the Invention

The present invention relates in general to pulse oximetry, and in particular to the processing of signals generated by a pulse oximeter.

2. Description of the Related Art

A pulse oximeter is typically used to measure various blood characteristics, including the blood oxygen saturation of hemoglobin in arterial blood and the pulse rate of the patient. Measurement of these characteristics has been accomplished by use of a non-invasive sensor that passes light through a portion of a patient's blood perfused tissue and photo-electrically senses the absorption and scattering of light in such tissue. The amount of light absorbed and scattered is then used to estimate the amount of blood constituent in the tissue using various algorithms known in the art. The "pulse" in pulse oximetry comes from the time varying amount of arterial blood in the tissue during a cardiac cycle. The signal processed from the sensed optical measurement is the familiar plethysmographic waveform, which corresponds with the cyclic attenuation of optical energy through a portion of a patient's blood perfused tissue.

Venous pulsation is an undesirable artifact in pulse oximetry. Venous pulsation is particularly common on the head or forehead, where the vascular anatomy lacks valves to prevent venous blood from backing up and pooling. Venous pulsation may be caused by the patient's medical condition, or during surgical interventions that interfere with venous return. The effects of venous pulsation may include: 1) oxygen saturation (e.g., $SpO_2$) readings reflecting a mix of venous and arterial blood, which would be substantially lower than the arterial oxygen saturation, thus resulting in incorrectly low oxygen saturation measurements, and 2) pulse rate readings that are double or even triple the patient's pulse rate, due to the prominent harmonics in the venous pressure wave. In addition, in extreme cases, it is possible that an oximeter would fail to acquire oxygen saturation and/or pulse rate measurements. Unlike motion artifacts that may be intermittent, venous pulsation can continue uninterrupted for hours. While the side effects of venous pulsation are highly visible to the clinician, their cause may not be.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a method for detecting venous pulsation. The method includes the act of deriving a skew metric for one or more plethysmographic signals. The presence of venous pulsation is detected based on the skew metric. Corresponding systems and tangible, machine readable media are also provided.

There is provided an additional method for detecting venous pulsation. The method includes the act of deriving a ratio of a minima-to-maxima time over an entire pulse period time of one or more plethysmographic signals. The presence of venous pulsation is detected based on the ratio. Corresponding systems and tangible, machine readable media are also provided.

There is provided a further method for detecting venous pulsation. The method includes the act of deriving a metric of the pulse shape of one or more plethysmographic signals. A phase comparison of the plethysmographic signals is also derived. The presence of venous pulsation is detected based on the metric of the pulse shape and the phase comparison. Corresponding systems and tangible, machine readable media are also provided.

BRIEF DESCRIPTION OF THE DRAWINGS

Advantages of the invention may become apparent upon reading the following detailed description and upon reference to the drawings in which:

FIG. 5 is a graph showing the results obtained in detecting venous pulsations according to an embodiment of the present invention.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present techniques relate to detection of venous or mixed venous and arterial pulsation in blood perfused tissue. The embodiments of the present invention provide methodologies, including software-based methods for detecting the venous pulsation artifact. The detection of the presence of venous pulsation enables an oximeter to notify a clinician, who could then address and/or correct the problem.

A pulse oximeter typically measures two physiological parameters, percent oxygen saturation of arterial blood hemoglobin ($SpO_2$) and pulse rate. Oxygen saturation can be estimated using various techniques. In one common technique, the photocurrent generated by the photo-detector may be conditioned and processed to determine the ratio of modulation ratios (ratio of ratios) of the red to infrared (IR) signals. This modulation ratio has been observed to correlate well to arterial oxygen saturation. Pulse oximeters and sensors may be empirically calibrated by measuring the modulation ratio over a range of in vivo measured arterial oxygen saturations (SpO$_2$) on a set of patients, healthy volunteers, or animals. The observed correlation may be used in an inverse manner to estimate blood oxygen saturation (SpO$_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING," issued Dec. 29, 1998, and U.S. Pat. No. 4,911,167, entitled "METHOD AND APPARATUS FOR DETECTING OPTICAL PULSES," issued Mar. 27, 1990, which are both herein incorporated by reference in their entirety for all purposes. The relationship between oxygen saturation and modulation ratio is described, for example, in U.S. Pat. No. 5,645,059, entitled "MEDICAL SENSOR WITH MODULATED ENCODING SCHEME," issued Jul. 8, 1997, which is herein incorporated by reference in its entirety for all purposes. Most pulse oximeters extract the plethysmographic signal having first determined saturation or pulse rate, both of which are susceptible to interference.

Figure 1:
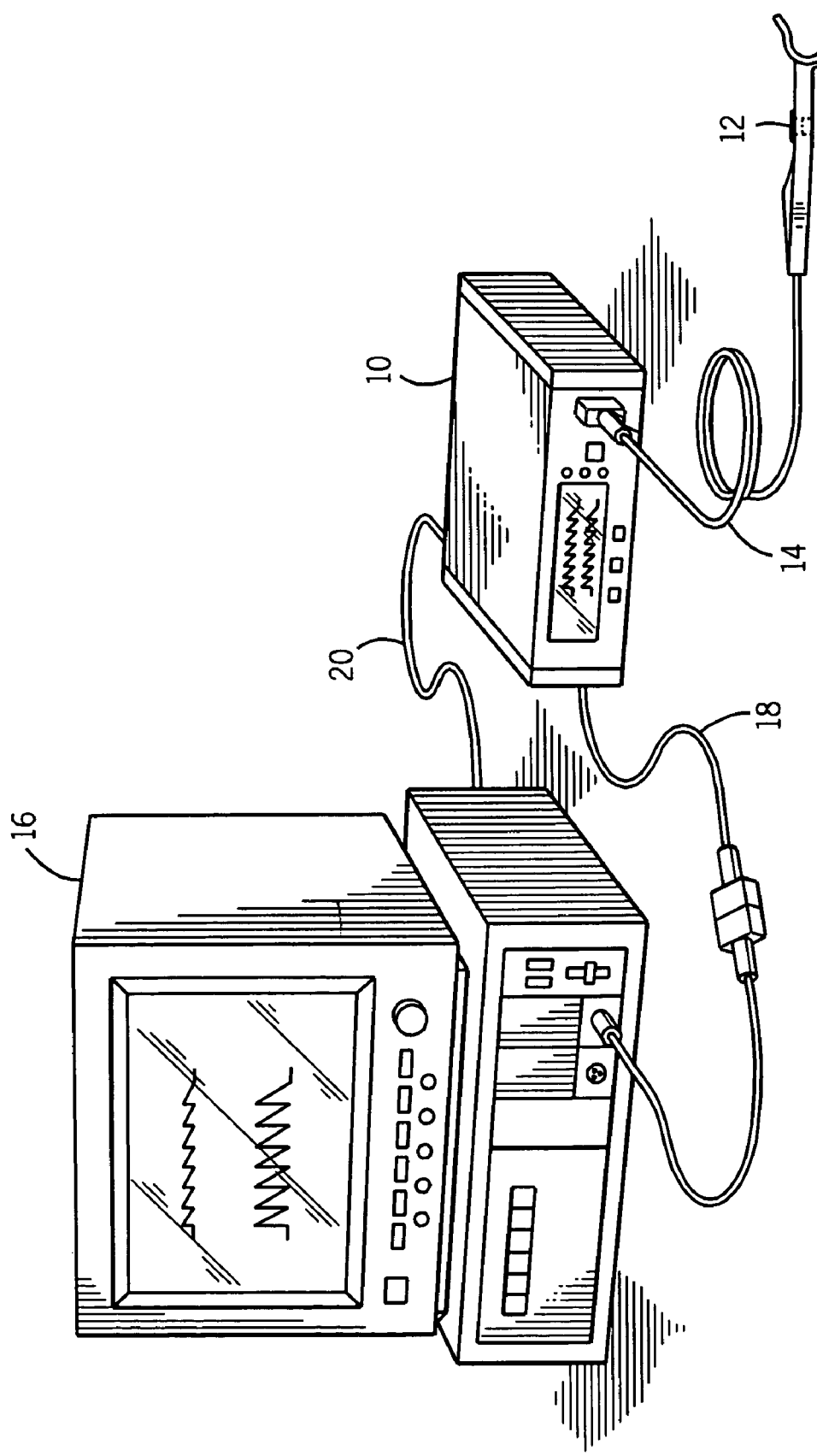
FIG. 1 illustrates a pulse oximetry system coupled to a multi-parameter patient monitor and a sensor according to embodiments of the present invention.

FIG. 1 illustrates one embodiment of a pulse oximetry system that may be configured to implement the embodiments of the present invention. A pulse oximetry monitor 10 may be used in conjunction with a sensor 12. It should be appreciated that the cable 14 of the sensor 12 may be coupled to the monitor 10 or it may be coupled to a transmission device (not shown) to facilitate wireless transmission between the sensor 12 and the monitor 10. The monitor 10 may be any suitable pulse oximeter, such as those available from Nellcor Puritan Bennett Inc. Furthermore, to upgrade conventional pulse oximetry provided by the monitor 10 to provide additional functions, the monitor 10 may be coupled to a multi-parameter patient monitor 16 via a cable 18 connected to a sensor input port or via a cable 20 connected to a digital communication port.

Figure 2:
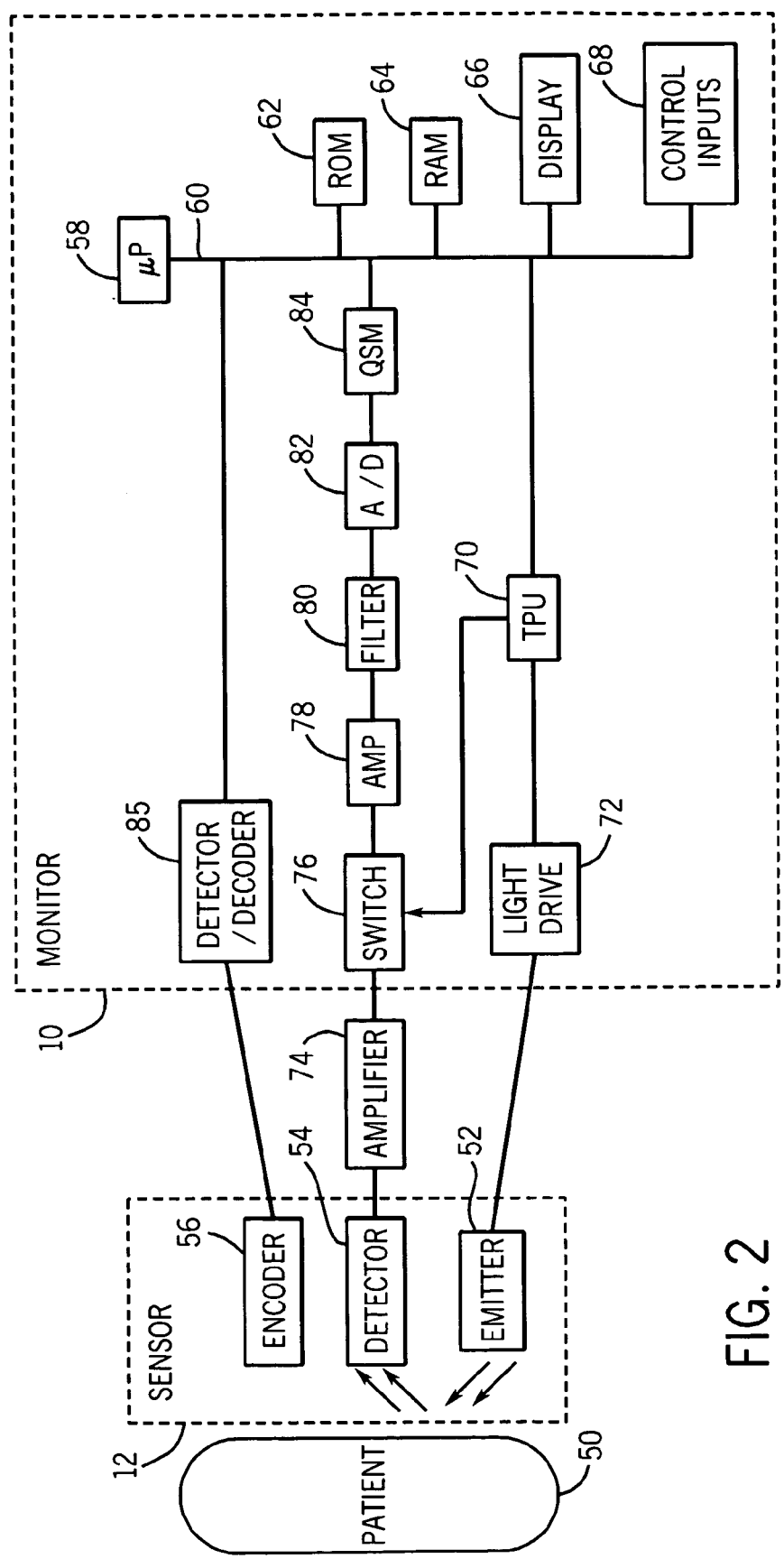
FIG. 2 is a block diagram of an exemplary pulse oximetry model connected to a sensor according to the present techniques.

FIG. 2 is a block diagram of one embodiment of a pulse oximeter that may be configured to implement the embodiments of the present invention. Sensor 12 may contain an emitter 52 and a detector 54. Light from an emitter 52 passes into blood perfused tissue of a patient 50 and is scattered then detected by a detector 54. The emitter 52 and the detector 54 may be disposed on a sensor body, which may be made of any suitable material, such as plastic, foam, woven material, or paper. Alternatively, the emitter 52 and the detector 54 may be remotely located and optically coupled to the sensor 12 using optical fibers. In the depicted embodiments, the sensor 12 is coupled to a cable 14 that is responsible for transmitting electrical and/or optical signals to and from the emitter 52 and detector 54 of the sensor 12. The cable 14 may be permanently coupled to the sensor 12, or it may be removably coupled to the sensor 12, the latter alternative being more useful and cost efficient in situations where the sensor 12 is disposable.

The sensor 12 may be a "transmission type" sensor. Transmission type sensors include an emitter 52 and detector 54 that are typically placed on opposing sides of the sensor site. If the sensor site is a fingertip, for example, the sensor 12 is positioned over the patient's fingertip such that the emitter 52 and detector 54 lie on either side of the patient's nail bed. In other words, the sensor 12 is positioned so that the emitter 52 is located on the patient's fingernail and the detector 54 is located 180° opposite the emitter 52 on the patient's finger pad. During operation, the emitter 52 shines one or more wavelengths of light through the patient's fingertip and the light received by the detector 54 is processed to determine various physiological characteristics of the patient. In each of the embodiments discussed herein, it should be understood that the locations of the emitter 52 and the detector 54 may be exchanged. For example, the detector 54 may be located at the top of the finger and the emitter 52 may be located underneath the finger. In either arrangement, the sensor 12 will perform in substantially the same manner.

Reflectance type sensors also operate by emitting light into the tissue and detecting the light that is transmitted and scattered by the tissue. However, reflectance type sensors include an emitter 52 and detector 54 that are typically placed on the same side of the sensor site. For example, a reflectance type sensor may be placed on a patient's fingertip or foot such that the emitter 52 and detector 54 lay side-by-side. Reflectance type sensors detect light photons that are scattered back to the detector 54. A sensor 12 may also be a "transflectance" sensor, such as a sensor that may subtend a portion of a baby's heel.

Emitter 52 and detector 54 may be of any suitable type. For example, the emitter 52 may be one or more light emitting diodes adapted to transmit one or more wavelengths of light in the red to infrared range, and the detector 54 may be one or more photodetectors selected to receive light in the range or ranges emitted from the emitter 52. Alternatively, emitter 52 may also be a laser diode or a vertical cavity surface emitting laser (VCSEL). Emitter 52 and detector 54 may also include optical fiber sensing elements. An emitter 52 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor 12 may sense light detected from the tissue at a different wavelength from the light emitted into the tissue. Such sensors may be adapted to sense fluorescence, phosphorescence, Raman scattering, Rayleigh scattering and multi-photon events or photoacoustic effects.

For pulse oximetry applications using either transmission or reflectance type sensors, the oxygen saturation of the patient's arterial blood may be determined using two or more wavelengths of light, most commonly red and near infrared wavelengths. Similarly, in other applications, a tissue water fraction (or other tissue constituent related metric) or a concentration of one or more biochemical components in an aqueous environment may be measured using two or more wavelengths of light. In certain embodiments, these wavelengths may be infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present techniques.

Sensor 12 containing emitter 52 and detector 54 may also contain an encoder 56 that provides signals indicative of the wavelength of emitter 52 to allow the oximeter to select appropriate calibration coefficients for calculating oxygen saturation. The encoder 56 may, for instance, be a resistor.

The sensor 12 may be connected to a pulse oximetry monitor 10. The monitor 10 includes a microprocessor 58 connected to an internal bus 60. Also connected to the bus are a read-only memory (ROM) 62, a random access memory (RAM) 64, a display 66, and control inputs 68. A time processing unit (TPU) 70 provides timing control signals to a light drive circuitry 72 which controls when the emitter 52 is illuminated, and if multiple light sources are used, the multiplexed timing for the different light sources. TPU 70 also controls the gating-in of signals from detector 54 through an amplifier 74 and a switching circuit 76. These signals are sampled at the proper time, depending upon which of multiple light sources is illuminated, if multiple light sources are used. The received signal from the detector 54 may be passed through an amplifier 78, a low pass filter 80, and an analog-to-digital converter 82. The digital data may then be stored in a queued serial module (QSM) 84, for later downloading to RAM 64 as QSM 84 fills up. In one embodiment, there may be multiple parallel paths of separate amplifier, filter and A/D converters for multiple light wavelengths or spectra received.

Based on the value of the received signals corresponding to the light received by detector 54, microprocessor 58 will calculate the oxygen saturation using various algorithms. These algorithms use coefficients, which may be empirically determined, corresponding to, for example, the wavelengths of light used. Signals indicative of the wavelengths of light used may be transmitted from the encoder 56 to a decoder 86. The decoder 86 translates these signals and determines which coefficients are needed for the various algorithms. These coefficients are stored in ROM 62. In a two-wavelength system, the particular set of coefficients chosen for any pair of wavelength spectra may be determined by the value indicated by the encoder 56 corresponding to a particular light source in a particular sensor 12. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 68. Control inputs 68 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter. These parameters may then be displayed on display 66. Additionally, in one embodiment of the present invention, a notification of venous pulsation may be displayed on display 66.

Figure 3:
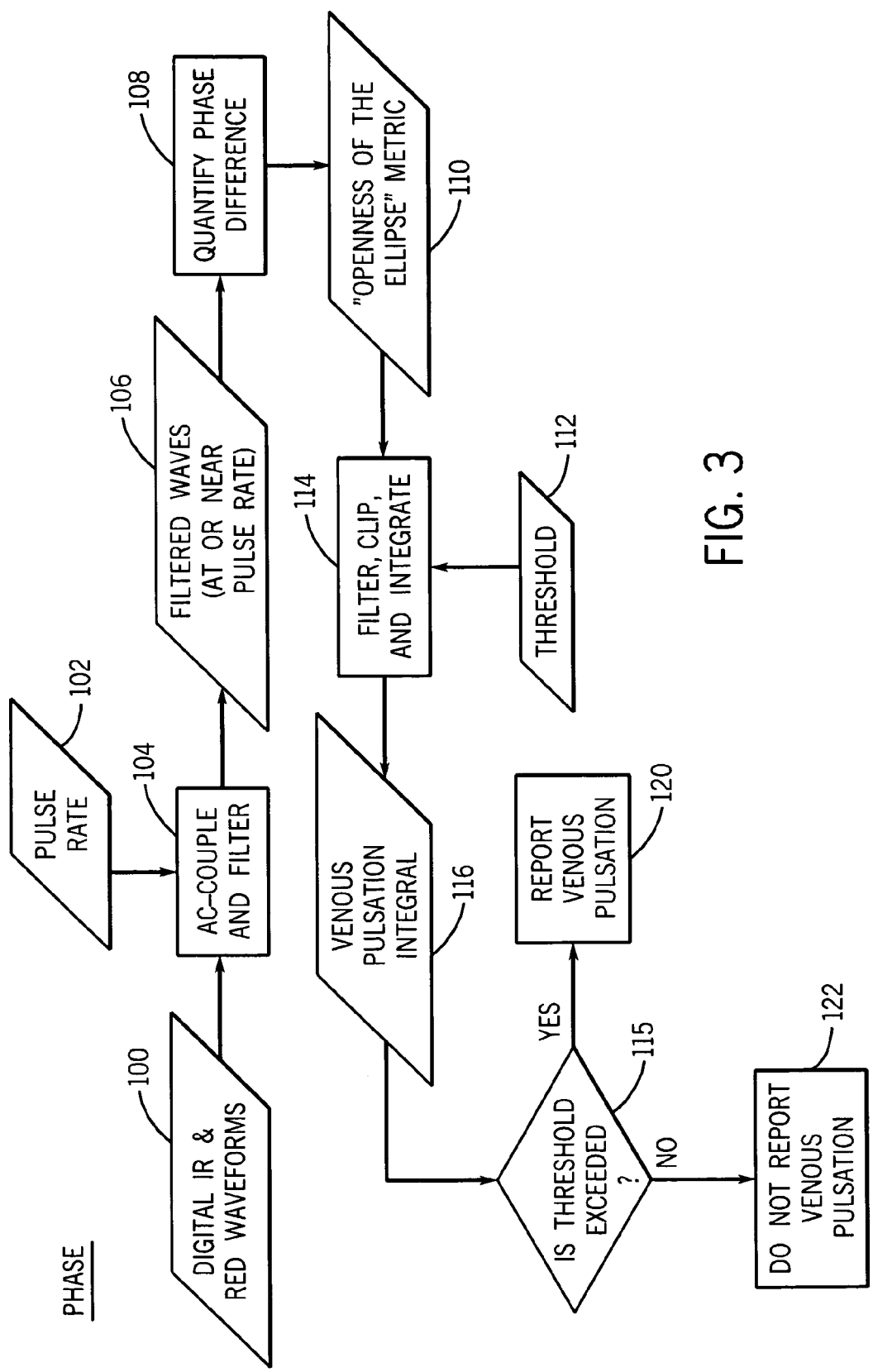
FIG. 3 is a flow chart of exemplary actions associated with detecting venous pulsations according to an embodiment of the present invention.

FIG. 3 is a flow chart illustrating the process by which venous pulsation may be detected using the phase difference between signal waveforms, according to one embodiment of the present invention. Mixed venous and arterial pulses may be distinguished from arterial pulses. First, venous blood has a lower saturation than arterial blood. Normoxic subjects (i.e., healthy subjects breathing air at sea level) who place their head significantly below their heart may readily create $SpO_2$ readings near 80% at the forehead if no pressure is applied to the sensor site. Second, the venous pulse occurs after the arterial pulse, and has a different shape. Due to these properties, the IR and red waveforms will have a significant and persistent phase difference if they include venous pulsation. On the other hand, the IR and red waveforms will be in-phase if they only include arterial pulses. The relationship between venous pulsation and waveform phase differences is described in U.S. Pat. App. Pub. No. 2005/0197579, entitled "METHOD AND APPARATUS FOR OPTICAL DETECTION OF MIXED VENOUS AND ARTERIAL BLOOD PULSATION IN TISSUE," published Sep. 8, 2005, which is herein incorporated by reference in its entirety for all purposes.

A waveform that may be better suited for detecting phase differences between IR and red waveforms is one that contains just the waveform corresponding to the fundamental of the pulse rate, such as may be produced by an appropriate filter. Such a waveform may be better suited for detecting phase differences between the IR and red waveforms that are of vascular origin. As illustrated in FIG. 3, one or more digital IR and red waveforms 100 are AC-coupled, so that they are both zero-mean, and filtered (Block 104) based on a pulse rate 102.

One or more filtered waveforms 106 may then be used to quantify the phase difference (Block 108), which may be characterized by the openness of the ellipse on a Lissajous plot. Over a time-window of at least one complete pulse, an "openness of the ellipse" metric 110 may be quantified as (minimum distance from the origin)/(maximum distance from the x-axis). Alternatively the denominator of this ratio may be the maximum distance from the origin. A longer time-window will increase the likelihood that motion artifact or Gaussian noise would eventually produce samples near the origin, and reduce the likelihood of falsely reporting venous pulsation. This "openness of the ellipse" metric 110 may be calculated as follows:

$$\text{Open\_Lissajous\_Axis\_Ratio} = \sqrt{\frac{\min((IR_t^2 + Red_t^2), (IR_{t-1}^2 + Red_{t-1}^2) \ldots (IR_{t-N+1}^2 + Red_{t-N+1}^2))}{\max(IR_t^2, IR_{t-1}^2 \ldots IR_{t-N+1}^2)}}$$

where IR and Red refer to the filtered waveforms 106 and N denotes the number of samples in the time-window.

In one embodiment, this metric may be computed periodically (e.g., every second) from the most recent time window (e.g., four seconds) of data. It therefore covers a window of about several pulses. A time window of about four seconds may assure that the waveforms have multiple pulse periods in which to come close to the origin if the waveforms are actually in-phase. The inclusion of the red data only in the numerator makes this metric more sensitive to out-of-phase waveforms at low saturations, where the red modulation is larger, than at high saturations.

Because the "openness of the ellipse" metric 110 may be fairly noisy, it may be filtered, clipped and integrated (Block 114) before being used to announce the presence or absence of venous pulsation. The filtering, clipping and integration are described below, such that a venous pulsation integral 116 may be calculated as follows:

$$w = \min\left(\frac{0.005}{|\text{Open\_Lissajous\_Axis\_Ratio} - \text{Open\_Lissajous\_Axis\_Ratio}'|}, 1.0\right)$$

Filt_Open_Lissajous_Axis_Ratio = $w *$ Open_Lissajous_Axis_Ratio +

$(1-w) *$ Filt_Open_Lissajous_Axis_Ratio$'$

Filt_Open_Lissajous_Axis_Ratio = min(Filt_Open_Lissajous_Axis_Ratio, 0.3)

Open_Lissajous_Threshold = max(0.06, 0.06 + 0.5 * (Saturation − 09.))

Venous_Pulsation_Integral = Venous_Pulsation_Integral$'$ +

Filt_Open_Lissajous_Axis_Ratio − Open_Lissajous_Threshold

Venous_Pulsation_Integral = min(2.0, max(0, Venous_Pulsation_Integral))

where "$'$" denotes the value from one second ago, and Saturation is the oxygen saturation value ($SpO_2$) scaled from zero to 1.0. The Open_Lissajous_Threshold metric controls how open the ellipse must be to eventually notify the user of venous pulsation. The threshold may vary with the calculated SpO$_2$, because venous pulsation is less likely to be occurring if high SpO$_2$ values are being calculated.

The venous pulsation integral 116 may be analyzed against a threshold to determine whether venous pulsation may be present (Block 118). In one embodiment, using the above approach, the presence of venous pulsation may be reported (Block 120) if the venous pulsation integral 116 is at least 1.0, and the presence of venous pulsation may not be reported (Block 122) if the integral 116 is less than 1.0.

Figure 4:
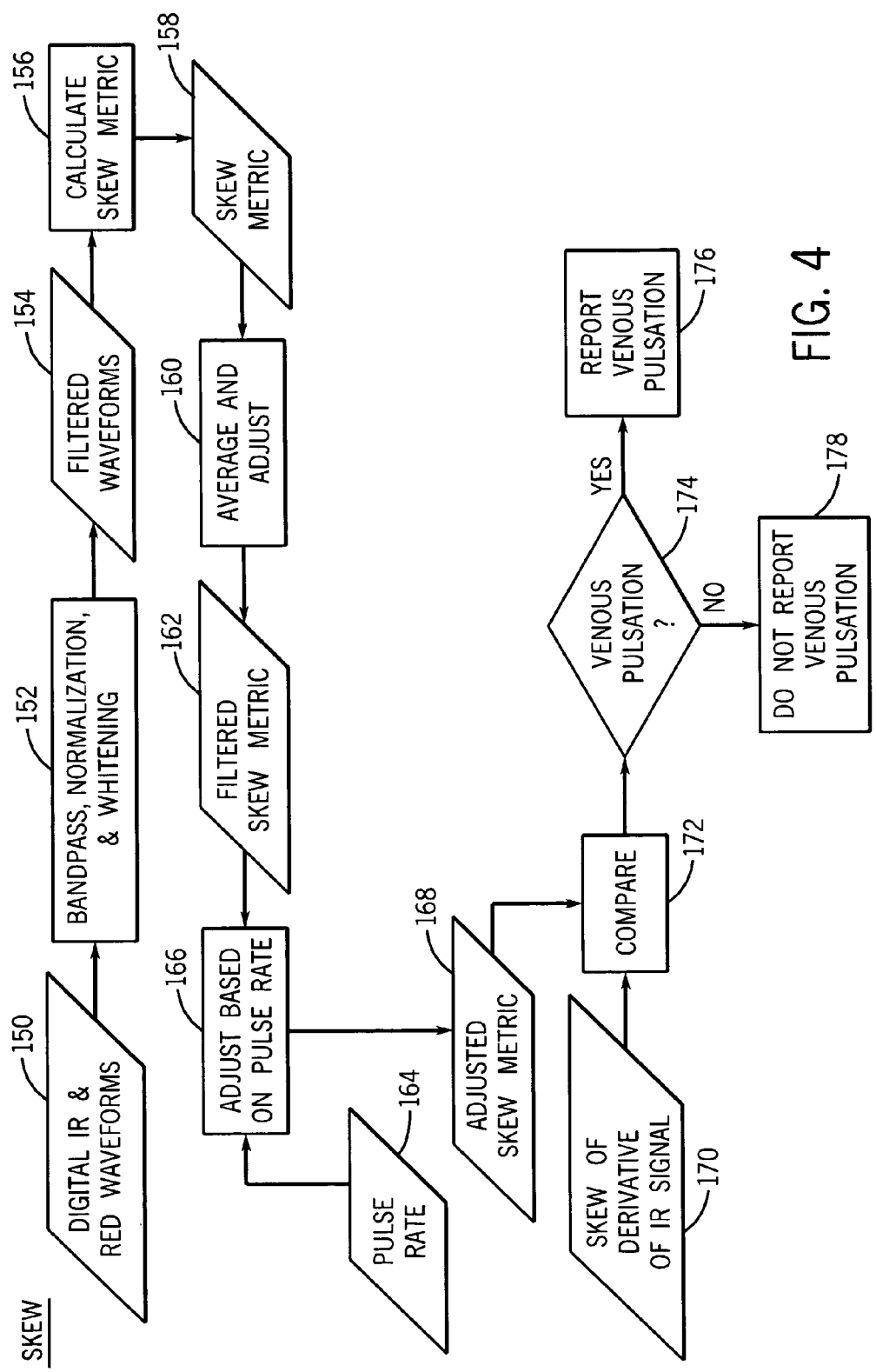
FIG. 4 is a flow chart of exemplary actions associated with detecting venous pulsations according to another embodiment of the present invention.

In accordance with another embodiment of the present invention, FIG. 4 is a flow chart illustrating the process by which venous pulsation may be detected using the skewness of the pulse shape. In the presence of only arterial pulsation, the photo-plethysmographic signal decreases quickly then increases slowly. In the presence of venous pulsation or a mixed arterial and venous pulsation, the signal decreases slowly and increases quickly. One pulse-shape metric that may be used to discriminate between these shape differences is the skewness of the derivative of the plethysmograph.

One or more digital IR and red waveforms 150 may be bandpassed, normalized, and whitened (Block 152) to produce one or more filtered waveforms 154. These filtered waveforms 154 may then be used to calculate (Block 156) a skew metric 158. Components of the skew metric 158 may be calculated as follows:

$$\text{IR\_Skew} = \frac{n \sum (x_t - \bar{x})^3}{(n-1)(n-2)\sigma^3}, \; x = IR_t + 2*(IR_t - IR_{t-1})$$

$$\text{Mixed\_Skew} = \frac{n \sum (x_t - \bar{x})^3}{(n-1)(n-2)\sigma^3},$$

$$x = (IR_t - c_1 * Red_t) + 2 * ((IR_t - c_1 * Red_t) - (IR_{t-1} - c_1 * Red_{t-1}))$$

where IR and Red refer to the filtered infrared waveforms 154, n is the number of samples in 3 seconds at the filter's sampling interval, $\sigma$ is standard deviation of x, and t is in samples. Using these components, the skew metric 158 may then be calculated as follows:

$$\text{Skew} = \left(1 - \frac{w}{0.55}\right) * \text{IR\_Skew} + \left(\frac{w}{0.55}\right) * \text{Mixed\_Skew}$$

where w is a mixing weight that may be varied between 0 and $c_1$ so as to reduce the Skew metric. In one embodiment, $c_1$ may have a value of 0.55.

The skew metric 158 may then be averaged and adjusted (Block 160) to compensate for typical rate-dependent changes in the skewness of human arterial waveforms. Because venous and arterial pulse shapes tend to have different derivatives of skewness with respect to rate, a filtered skew metric 162 may be further adjusted (Block 166) based on a pulse rate 164, according to the following calculation:

$$\text{Adj\_Skew} = \max\left(\text{Filt\_Skew}, \text{Filt\_Skew} + 0.6 * \frac{\text{Rate} - 100.0}{\text{Rate}}\right)$$

where Filt_Skew is the filtered skew metric 162, Rate is the pulse rate 164, and Adj_Skew is an adjusted skew metric 168.

The adjusted skew metric 168 may then be further adjusted (Block 172) based on a comparison to the skewness of the derivative of the IR plethysmographic signal 170 according to the following calculation:

$$\text{Adj\_Skew} = \frac{\min(\text{Adj\_Skew}, \text{Deriv\_Skew} + 0.8)}{6.0}$$

where Deriv_Skew is the skewness of the derivative of the IR plethysmograph 170.

Venous pulsation may then be detected (Block 174) if the adjusted skew metric determined by the comparison 172 exceeds a predetermined threshold. In one embodiment, venous pulsation may be reported when it has been detected, and not reported if the adjusted skew metric determined by the comparison 172 goes below a predetermined threshold, such as an empirically determined threshold.

In an alternative embodiment of the present invention, the presence of venous pulsation may be detected using the time ratio metric quantified as (minima-to-maxima time of the plethysmographic signal)/(entire pulse period). In this embodiment, the presence of venous pulsation may be reported if the ratio of minima-to-maxima time over the entire pulse period is less than a predetermined threshold, such as an empirically determined threshold.

In a further embodiment of the present invention, the "openness of the ellipse" metric 100 and adjusted skew metric 168 described in relation to FIGS. 3 and 4 may be combined to assess the presence of venous pulsation. This assessment may be performed using the following calculations:

$$\text{VP\_Metrics\_Threshold} = \max(0.00, 0.00 + 0.4 * (\text{Saturation} - 0.9))$$

$$w = \min(\text{Pulse\_Amp\_Ratio}, 1.0)$$

Venous_Pulsation_Integral =

$$\text{Venous\_Pulsation\_Integral}' + w * (\text{Filt\_Open\_Lissajous\_Axis\_Ratio} +$$
$$\text{Adj\_Skew} - \text{VP\_Metrics\_Threshold})$$

$$\text{Venous\_Pulsation\_Integral} = \max(0, \min(2.0, \text{Venous\_Pulsation\_Integral}))$$

where "'" denotes the value from one second ago, Saturation is the oxygen saturation value (SpO$_2$) and Pulse_Amp_Ratio is the ratio of current pulse amplitude to historical pulse amplitude.

The presence of venous pulsation may be reported if the venous pulsation integral is at least 1.0, and the presence of venous pulsation may not be reported if the integral is less than 1.0. This combined phase and shape metric may produce results better than those produced with either single metric, as shown in FIG. 5.

FIG. 5 is a graphic illustration of a simplified set of results of trials testing the detection of venous pulsation. An axis 200 depicts the shape metric and an axis 202 depicts the phase metric. Good data points 204 represent the patient trials where digit (arterial) and forehead (possibly arterial and/or venous) SpO$_2$ measurements agreed to within 4-5 points. Bad data points 206 represent the patient trials where digit and forehead SpO$_2$ measurements were more discrepant.

A horizontal line 208 depicts the venous pulsation classification threshold using only the phase metric, according to one embodiment of the present invention, such that venous pulsation would be detected for phase metric readings above the line 208. A vertical line 210 depicts the venous pulsation classification threshold using only the skew metric, according to another embodiment of the present invention, such that venous pulsation would be detected for shape metric readings to the right of the line 210. A diagonal line 212 depicts the venous pulsation classification threshold using a combination of the phase and skew metrics according to a further embodiment of the present invention.

It can be seen from this graph that venous pulsation has a higher incidence of being indicated using a combination of the phase and metrics than using either metric alone. In addition, where venous pulsation is not occurring, there is a lower incidence of incorrect notification when both phase and shape metrics are used.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized in conjunction with the measurement and/or analysis of carboxyhemoglobin, methemoglobin, total hemoglobin, intravascular dyes, and/or water content. Likewise, the technique may be employed using other techniques for measuring pulse shape, different sequences of filtering, different constants, and so forth. The invention is to cover all modifications, equivalents, and alternatives falling within the spirit and scope of the invention as defined by the following appended claims.

What is claimed is:

1. A method for detecting venous pulsation with a patient monitor having a microprocessor, comprising:
   deriving a skew metric for one or more plethysmographic signals with the microprocessor; wherein the skew metric comprises a measure of the skewness of the derivative of the one or more plethysmographic signals;
   filtering the skew metric based on a first set of filters with the microprocessor to generate a filtered skew metric;
   adjusting the filtered skew metric with the microprocessor based on a pulse rate to generate an adjusted skew metric;
   detecting the presence of venous pulsation with the microprocessor by comparing the adjusted skew metric to a predetermined threshold.

2. The method of claim 1, wherein the skew metric is processed to compensate for the typical rate-dependent changes in the skewness of arterial waveforms.

3. The method of claim 1, further comprising providing a notification of the presence of venous pulsation when detected.

4. One or more non-transitory machine readable media, comprising code executable by a microprocessor to perform the acts of:
   deriving a skew metric for one or more plethysmographic signals wherein the skew metric comprises a measure of the skewness of the derivative of the one of more plethysmographic signals;
   filtering the skew metric based on a first set of filters to generate a filtered skew metric;
   adjusting the filtered skew metric based on a pulse rate to generate an adjusted skew metric; and
   detecting the presence of venous pulsation by comparing the adjusted skew metric to a predetermined threshold.

5. The non-transitory, machine readable media of claim 4, further comprising code executable by the microprocessor to perform the act of processing the skew metric to compensate for the typical rate-dependent changes in the skewness of arterial waveforms.

6. The non-transitory, machine readable media of claim 4, further comprising code executable by the microprocessor to perform the acts of providing a notification of the presence of venous pulsation when detected.

7. A patient monitoring system comprising: a patient monitor configured to:
   derive a skew metric for one or more plethysmographic signals wherein the skew metric comprises a measure of the skewness of the derivative of the one or more plethysmographic signals;
   filter the skew metric based on a first set of filters to generate a filtered skew metric;
   adjust the filtered skew metric based on a pulse rate to generate an adjusted skew metric; and
   detect the presence of venous pulsation by comparing the adjusted skew metric to a predetermined threshold.

8. The system of claim 7, wherein the patient monitor is configured to process the skew metric to compensate for the typical rate-dependent changes in the skewness of arterial waveforms.

9. The system of claim 7, wherein the patient monitor is configured to provide a notification of the presence of venous pulsation when detected.

* * * * *